(12) United States Patent
Lee et al.

(10) Patent No.: US 8,101,894 B2
(45) Date of Patent: Jan. 24, 2012

(54) COOKING DEVICE WITH DEODORIZATION

(75) Inventors: Won Hui Lee, Seoul (KR); Hyun Jung Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 544 days.

(21) Appl. No.: 12/234,964

(22) Filed: Sep. 22, 2008

(65) Prior Publication Data

US 2009/0110592 A1 Apr. 30, 2009

(30) Foreign Application Priority Data

Oct. 29, 2007 (KR) .................. 10-2007-0108962

(51) Int. Cl.
*H05B 6/68* (2006.01)
*F24C 15/30* (2006.01)
*F24C 15/00* (2006.01)

(52) U.S. Cl. .................... 219/757; 126/19 R; 126/21 R; 126/21 A; 126/299 R; 422/5

(58) Field of Classification Search .................. 219/757, 219/756, 707, 400, 681, 685; 422/5, 4, 23, 422/121, 906, 30; 126/21 A, 21 R, 299 R, 126/19 R
See application file for complete search history.

(56) References Cited

U.S. PATENT DOCUMENTS

| 2007/0158328 A1 | 7/2007 | Kim et al. |
| 2008/0099475 A1 | 5/2008 | Lee et al. |
| 2008/0121635 A1 | 5/2008 | Lee |

FOREIGN PATENT DOCUMENTS

| KR | 10-1995-0010380 B1 | 9/1995 |
| KR | 10-2000-0056754 A | 9/2000 |
| KR | 10-2003-0071677 A | 9/2003 |
| KR | 20-0315698 Y1 | 9/2003 |
| KR | 10-0712269 B1 | 4/2007 |

OTHER PUBLICATIONS

U.S. Appl. No. 12/234,841 to Sim et al, which was filed Sep. 22, 2008.

*Primary Examiner* — Quang Van
(74) *Attorney, Agent, or Firm* — Birch, Stewart, Kolasch & Birch, LLP

(57) ABSTRACT

A cooking device includes an inner case, a cooking chamber within the inner case and an odor removal unit configured to generate a plasma discharge for removing odor-producing materials from the cooking chamber.

17 Claims, 6 Drawing Sheets

COOKING DEVICE WITH DEODORIZATION

This application claims the benefit of Korean Patent Application No. 10-2007-0108962, filed on Oct. 29, 2007, which is hereby incorporated by reference for all purposes as if fully set forth herein.

BACKGROUND OF THE INVENTION

1. Field of the Invention

The present invention relates to a cooking device, and more particularly, to a cooking device which can remove odor and odor-producing materials from a cooking chamber.

2. Description of the Related Art

In a conventional cooking device, odor and odor-producing materials escape from the cooking device when cooked food is removed from the cooking device. Such a odors may give users an unpleasant experience, especially when the food is fish.

SUMMARY OF THE INVENTION

An aspect of the present invention provides a cooking device that is capable of removing the odor and odor-producing materials from cooking space in the cooking device.

According to an aspect of the present invention, a cooking device includes an inner case; a cooking chamber within the inner case; and an odor removal unit configured to generate a plasma discharge for removing odor-producing materials from the cooking chamber.

The plasma discharge may generate ozone and/or ions for removing the odor-producing materials. The inner case may include an opening for exhausting air containing odor-producing materials from the cooking chamber to the outside, and the odor removal unit may be arranged to correspond to the opening. The odor-producing materials may be removed from the air while passing through the odor removal unit, after which the air is mixed with air from the outside, and then discharged to the outside.

The cooking device may further include an outer case containing the inner case and the odor removal unit, wherein air containing odor-producing materials circulates in the outer case, so that the odor-producing materials are removed from the air while passing through the odor removal unit. The inner case may include a first opening for arranging the odor removal unit and a second opening connecting the cooking chamber with the outside of the cooking chamber. The air may be discharged to the outside of the cooking chamber through the first opening, and then return to the inside of the cooking chamber through the second opening. The second opening may be configured to be closed during cooking of food in the cooking chamber so as not to return air to the inside of the cooking chamber, and opened before or after cooking so as to return air to the inside of the cooking chamber. The cooking device may further include a first valve configured to selectively open and close the first opening; and a second valve configured to selectively open and close the second opening.

The cooking device may further include a controller that selectively controls the operation of the odor removal unit. The controller may automatically operate the odor removal unit based on cooking information of the food. The cooking information may include a plurality of cooking modes of the cooking device, and the controller may automatically operate the odor removal unit based on the plurality of cooking modes. The cooking plurality of cooking modes may be classified into a plurality of groups based on the expected discharge amount of the odor-producing materials, such that for groups having a relatively large expected discharge amount of the odor-producing materials, the controller increases the duration of the operation time of the odor removal unit and/or increases the amount of power supplied to the odor removal unit.

The cooking device may further include an input unit configured to receive instructions input by a user; and a controller operating the odor removal unit based on the instructions input through the input unit. The cooking device may further include an ozone removal unit configured to remove residual ozone remaining in the air downstream from the odor removal unit.

The odor removal unit may include a first discharge electrode and a second discharge electrode spaced from each other to generate the plasma discharge, and a dielectric layer interposed between the first discharge electrode and the second discharge electrode. The first discharge electrode may be applied with a voltage, and the second discharge electrode may be grounded. The cooking device may be a microwave oven.

According to another aspect of the present invention, a method for deodorizing air in a cooking device includes exhausting air containing odor-producing materials from a cooking chamber of the cooking device through a first opening; and selectively deodorizing air passing through the first opening by removing the odor-producing materials.

The selectively deodorizing the air may include generating plasma discharge to produce ozone and/or ions for removing the odor-producing materials from the air. The method may further include removing residual ozone remaining in the air. The method may further include selectively re-circulating the air back into the cooking chamber through a second opening. The selectively re-circulating the air may include closing the second opening while food is being cooked in the cooking chamber, and opening the second opening when food is not being cooked in the cooking chamber.

The selectively deodorizing the air may include automatically deodorizing the air based on a cooking mode of the cooking device. The selectively deodorizing the air may include deodorizing the air based on a selection input by a user.

According to the exemplary embodiments of the present invention, the odor and odor-producing materials from the cooking space may be effectively removed through a plasma discharge generated by the odor removal unit.

BRIEF DESCRIPTION OF THE DRAWINGS

The above and other aspects, features and advantages of the present invention will be more apparent from the following detailed description taken in conjunction with the accompanying drawings, in which.

DETAILED DESCRIPTION OF THE PREFERRED EMBODIMENT

Hereinafter, exemplary embodiments of the present invention of will be described with reference to accompanying drawings.

The deodorization device of the present invention may be applied to any suitable type of cooking apparatus, such as a gas, electric or microwave oven. Further, the cooking apparatus of the present invention may include all kinds of devices capable of cooking food, such as a gas, electric or microwave oven.

Figure 1:
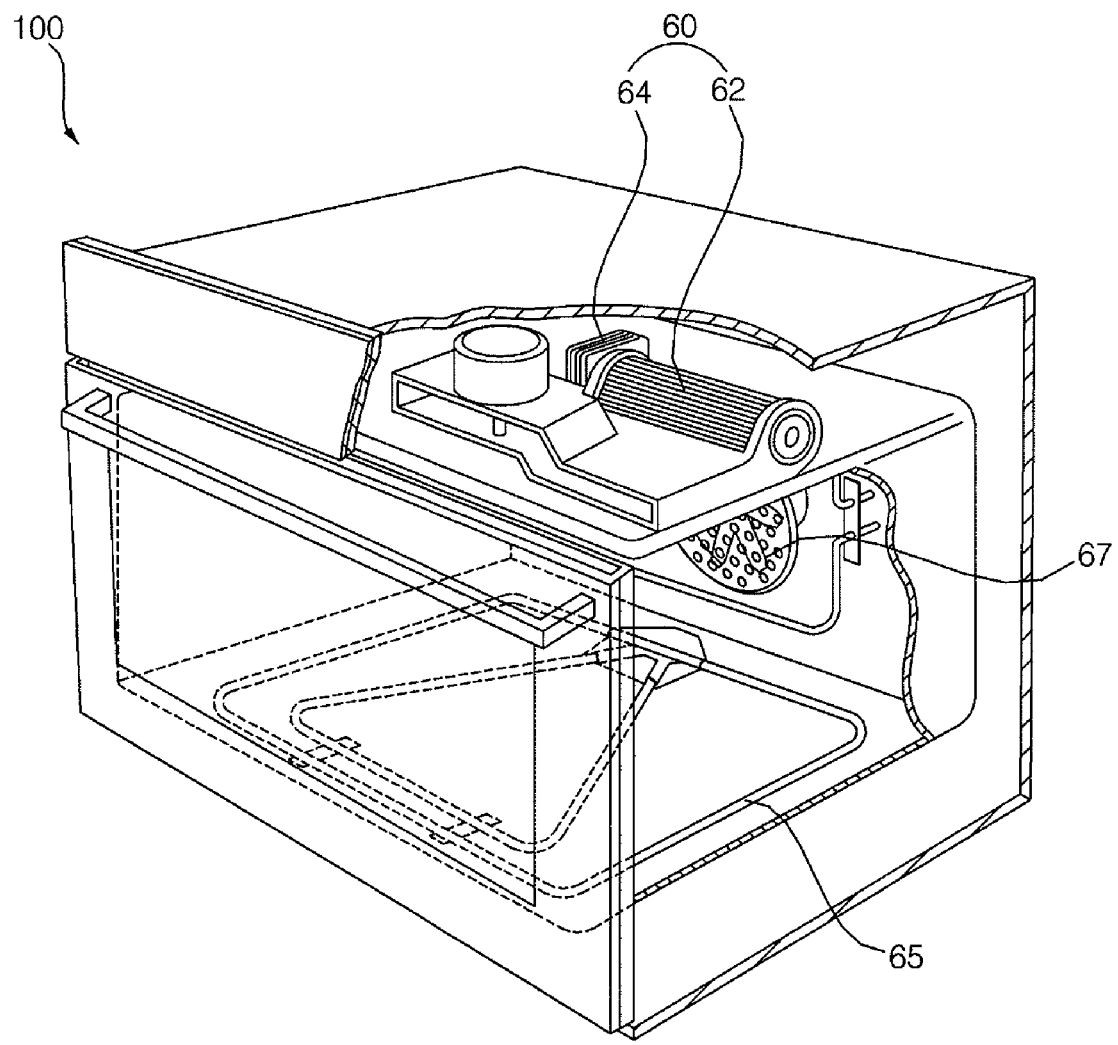
FIG. 1 is a partially exploded perspective view of a cooking device according to an exemplary embodiment of the present invention.
Figure 2:
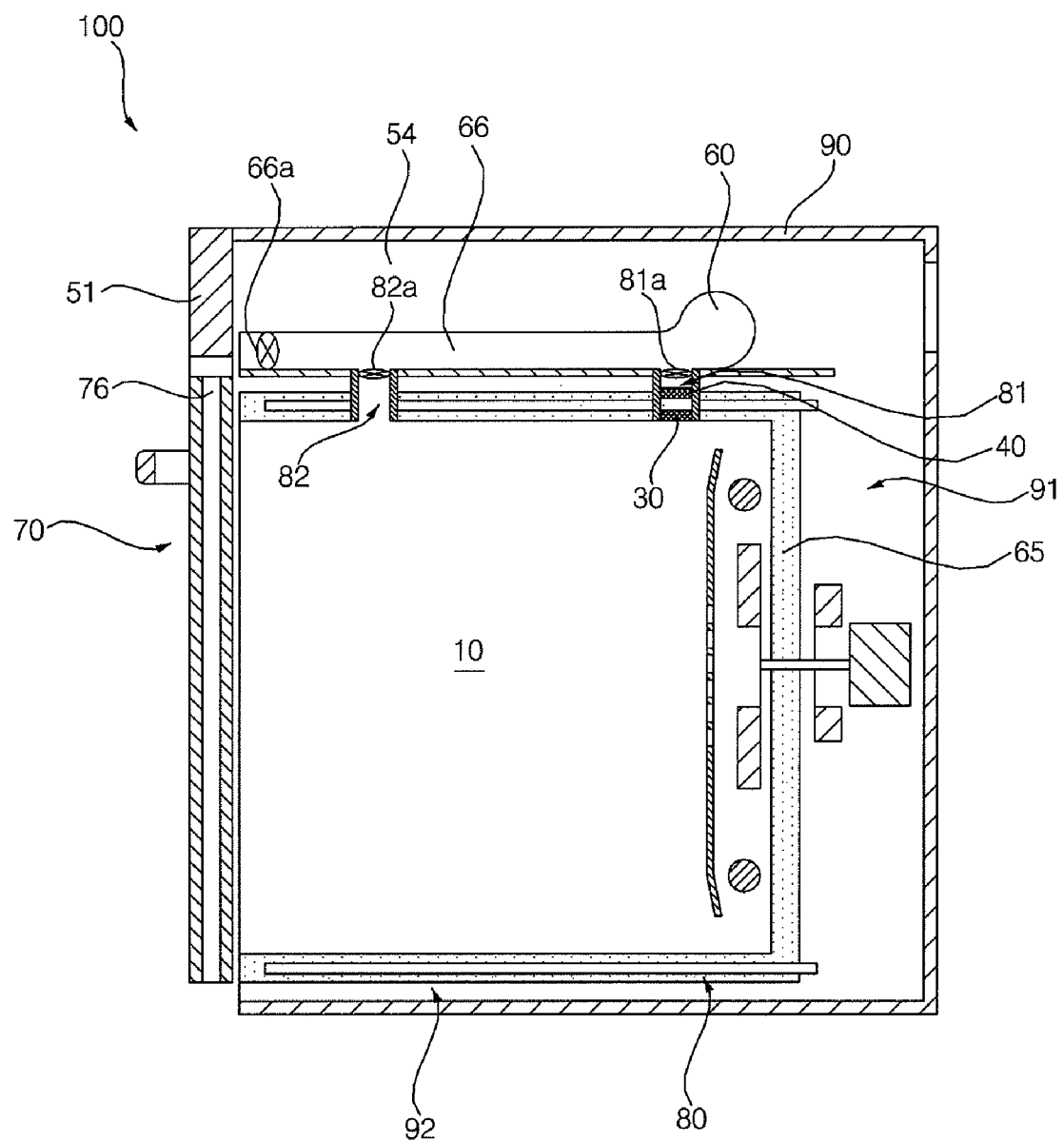
FIG. 2 is a cross sectional view showing an inner structure of the cooking device of FIG. 1.

FIG. 1 is a partially exploded perspective view of a cooking device according to an exemplary embodiment of the present invention, and FIG. 2 is a cross sectional view showing an inner structure of the cooking device of FIG. 1. Referring to FIGS. 1 and 2, the cooking device 100 includes an inner case 80 and an outer case 90. The inner case 80 defines cooking space or chamber 10 for cooking food. The outer case 90 partitions space containing the inner case 80, an electric components room 54 located above the inner case 80, a rear air passage 91 located on the rear side of the inner case 80, and a lower air passage 92 located on the lower side of the inner case 80.

As shown in FIG. 2, a door 70 is arranged on the outer case 90 to open and close the cooking space 10. The door 70 is connected with the outer case 90 in any suitable manner to open and close the cooking space 10, such as by pivoting on a hinge. The door 70 may have any suitable structure, such as a plurality of plate members, which are spaced from each other to provide a flow path 76 for cooling air inside the door.

As shown in FIG. 1, a heater 65 is arranged on the upper side, lower side, and rear side of the cooking space 10 to heat the cooking space 10. Also, a cooking chamber fan 67 is arranged on the rear side of the cooking space 10. The cooking chamber fan 67 sucks the air from the inside of the cooking space 10, heats the sucked air by the heater 65 mounted in the rear side of the cooking space 10, and then discharges the heated air toward the inside of the cooking space 10.

A blower module 60 is arranged in the electric components room 54, as shown in FIGS. 1 and 2. The blower module 60 includes a fan 62 for generating a flow of air inside of the rear air passage 91 and a motor 64 for driving the fan 62.

A duct 66 is arranged in the electric components room 54 and connected with an outlet of the blower module 60. The duct 66 includes a duct valve 66a for opening and closing the duct 66. The inner case 80 includes a first communicating portion or opening 81 which connects the cooking space 10 with the duct 66. The first communicating portion 81 includes a first valve 81a for opening and closing the first communicating portion 81. The inner case 80 includes a second communicating portion or opening 82. The second communicating portion 82 connects the cooking space 10 with the duct 66, and is located in the lower side of the duct 66 forward of the first communicating portion 81. The second communicating portion 82 includes a second valve 82a for opening and closing the second communicating portion 82.

The blower module 60 sucks the air from the outside to the inside of the electric components room, cools the electric components room 54, and then discharges the air to the outside. The air discharged from the duct 66 to the outside is exhausted through space between the upper side of the door 70 and the front plate 51 of the outer case 90. However, the air sucked in the blower module 60 may also flow into the cooking space 10 through the second communicating portion 82.

The cooking device 100 includes a odor removal unit 30. The odor removal unit 30 is arranged in the first communicating portion 81, and serves to remove the odor and odor-producing materials from the cooking space 10. The arrangement of the odor removal unit 30 is not limited to the above, but instead the odor removal unit 30 may be located at any position through which air containing odor and odor-producing materials flows.

Figure 3:
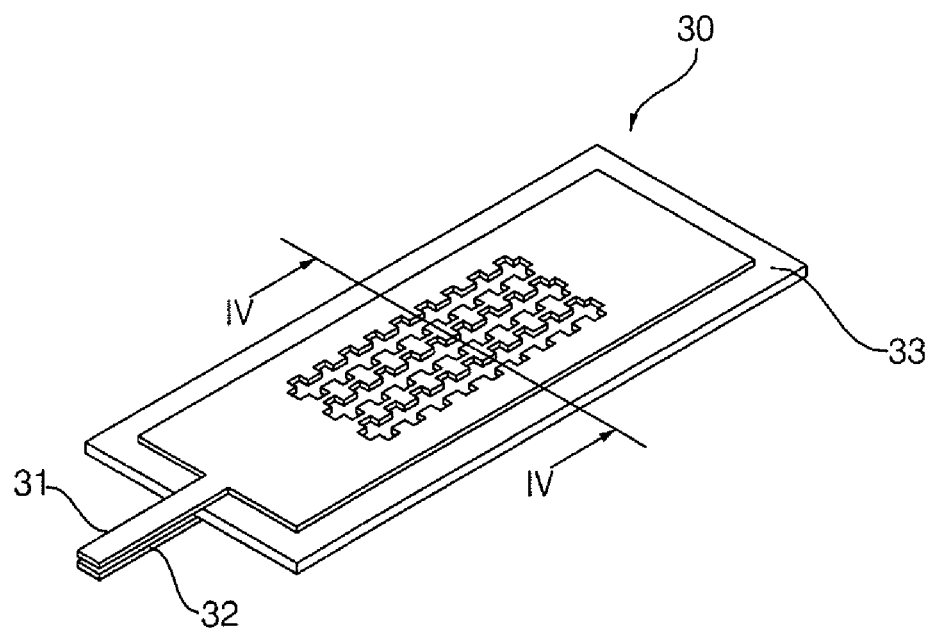
FIG. 3 is a partial perspective view of a odor removal unit shown in FIG. 2.
Figure 4:
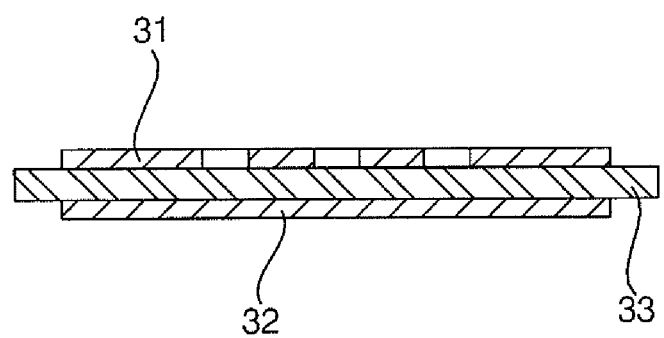
FIG. 4 is a cross sectional view taken along line IV-IV of FIG. 3.

The odor removal unit 30 produces plasma to generate ozone and ions. The odor removal unit 30, which is shown in FIGS. 3 and 4, may have any suitable configuration. FIG. 3 is a partial perspective view of the odor removal unit 30, and FIG. 4 is a cross sectional view taken along line IV-IV of FIG. 3. Referring to FIGS. 3 and 4, the odor removal unit 30 includes a first discharge electrode 31, a second discharge electrode 32, a dielectric layer 33, and any suitable type of power supply (not shown). The first discharge electrode 31 and the second discharge electrode 32 are spaced from each other, with the dielectric layer 33 interposed therebetween. A discharge voltage is applied to the first discharge electrode 31 by the power supply, and the second discharge electrode 32 is grounded. However, the construction of the odor removal unit 30 is not limited to the above.

An ozone removal unit 40 is arranged behind the odor and odor-producing materials removal unit 30 in the first communicating portion 81. The ozone removal unit 40 eliminates the remaining ozone flowing from the odor removal unit 30. Though ozone is used to effectively remove odor and odor-producing materials, there is a danger that ozone may be harmful to human health when it is discharged to the outside. Accordingly, it is necessary to control the amount of ozone discharged to a set value or less. The ozone removal unit 170 breaks ozone down by heating the gas, introduced from the second deodorization region 142, to a set temperature or higher. However, the ozone removal unit is not limited to the structure described above, but the ozone removal unit 170 may remove ozone in any suitable manner. Also, the ozone removal unit 40 is not necessarily required in the cooking device 100. While the cooking device 100 operates for cooking, the temperature of air flowing through the first communicating portion 81 becomes very high. Accordingly, the ozone mixed in the air may be removed by being heated while the ozone is flowing with high-temperature air. In a case where the ozone removal unit 40 is provided, the ozone may be more effectively removed.

Figure 5:
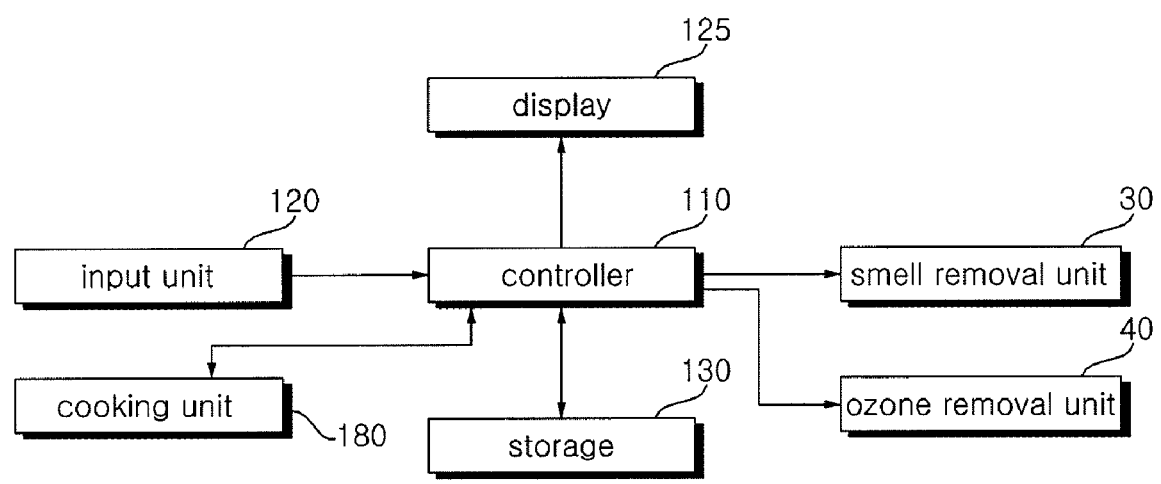
FIG. 5 is a block diagram showing a flow of a control signal of the cooking device of FIG. 1.

FIG. 5 is a block diagram showing a flow of a control signal of the cooking device of FIG. 100. Referring to FIG. 5, an input unit 120 receives an operation signal from a user, and a cooking unit 180 cooks food based on the operation signal input by the user. The cooking unit 180 includes the heater 65, the cooking chamber fan 67, the first valve 81a, the second valve 82a, and the duct valve 66a. However, the cooking unit 180 may cook food in any suitable manner, such as with heat from a heating element or with microwaves. The input unit 120 may have any suitable structure, such as a button or a dial.

A storage 130 stores information related to operation of the cooking device 100. If an operation signal is input by a user, a controller 110 generates a control signal based on the operation signal and transmits the control signal to the heater 65 and room fan 67. The heater 65 and room fan 67 cook food according to the control signal. A display 125, which may have any suitable structure, such as an LCD panel, may display any suitable information, such as cooking information of food or a user's operation information.

Figure 6:
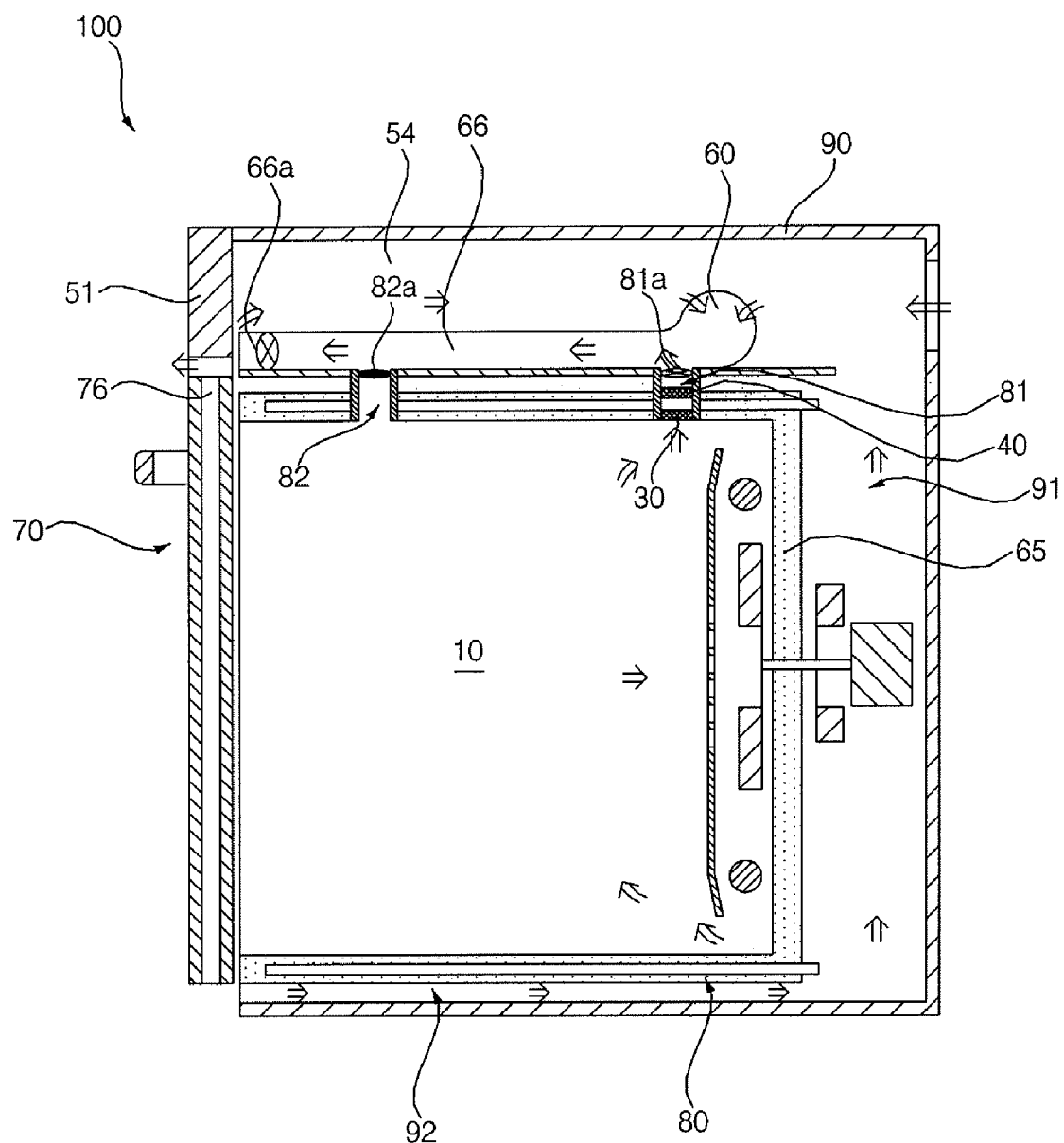
FIG. 6 is a view schematically illustrating a circulation of air in the cooking device of FIG. 2 during cooking.

Hereinafter, a mechanism for eliminating the odor and odor-producing materials from the cooking device 100 will be described in more detail. FIG. 6 shows a circulation structure of gas or air in the cooking device 100 during cooking. Herein, 'gas' or 'air' includes air or gas and/or particles that generate the odor. The cooking device 100 cooks food in various cooking modes. The cooking modes may include a warming mode, a defrosting mode, and a roasting mode. When the food is cooked in the roasting mode, a relatively large amount of odor and odor-producing materials are generated in the cooking space 10. In contrast, when the food is cooked in the defrosting mode, a relatively small amount of odor and odor-producing materials (or none) are generated in the cooking space 10. Accordingly, the cooking modes may be classified in several groups based on the expected amount of odor and odor-producing materials generated. The groups may include a 'strong' group, a 'normal' group, and a 'weak' group. In the cooking modes included in the strong group, the operation time of the odor removal unit 30 may be lengthened or the amount of plasma generated may be increased, such as by increasing the power supplied to the odor removal unit, to remove more odor and odor-producing materials. In the cooking modes included in the weak group, the operation of the odor removal unit 30 may be stopped. In the normal group, the odor removal unit 30 still operates, however, its operation time may be set up to be shorter than in the strong group or the amount of plasma generated may be reduced, such as by decreasing the power supplied to the odor removal unit.

The operation time period of the odor and odor-producing materials removal unit 30 may be manually adjusted. The input unit 120 may receive an operation signal from a user, and the controller 110 may change the operation time period of the odor removal unit 30 according to the operation signal.

When the odor removal unit 30 operates, the ozone removal unit 40 operates accordingly. The ozone removal unit 40 may be operated in communication with the odor and odor-producing materials removal unit 30, and may also be operated only when the operation mode is set as the strong group. Furthermore, the ozone removal unit 40 may be manually operated by a user.

Referring to FIG. 6, odor and odor-producing materials are produced when the food is cooked in the cooking space 10. At this time, the fan 62 operates to cool the electric components room 54. As a result, the external air is flowed in the lower passage 92 and rear passage 91 of the cooking device 100. The first valve 81a opens, the second valve 82a closes, and the duct valve 66a opens. The temperature inside of the cooking space 10 increases, the odor and odor-producing materials are mixed with the air inside of the cooking space 10, and the mixed gas is flowed in the first communicating portion 81. Furthermore, when the fan 62 is operated, the gas from inside the cooking space 10, which communicates with the fan 62, is more briskly flowed in the first communicating portion 81.

The odor removal unit 30 operates in the first communicating portion 81 to generate a plasma discharge. During the plasma discharge, ozone and ions are produced from air. At this time, various types of ions may be produced. The ions may include negative ions, such as OH—. The ions and ozone reacts with the odor and odor-producing materials to dissolve and remove the odor and odor-producing materials. A main source material of the odor and odor-producing materials is a mixture of C—H, wherein the ions and ozone disconnect C—H bond in the source material. The amount of removed odor and odor-producing materials is determined depending on the amount of generated ions and ozone, the reaction time of the odor and odor-producing materials, and the like.

Furthermore, the moisture is condensed and small aerosol particles are produced during the plasma discharge, and the condensed moisture and produced small aerosol particles play a role to remove the odor and odor-producing materials. Especially, the small aerosol particles directly react with the material that generates the odor and odor-producing materials thereby to produce a large quantity of $CH_3$—S radicals. The $CH_3$—S radicals disconnect the C—H bond, thus removing the odor and odor-producing materials.

The gas from which the material that generates the odor is removed is mixed with external air that flows in the inside of the electric components room 54, and then the mixed gas is discharged to the outside through the duct 66. The gas flowing in the first communicating portion 81 from the cooking space 10 is in a high temperature condition. Therefore, the remaining ozone may be dissolved naturally by such high temperature, as well as by the ozone removal unit 40.

In the cooking device 100 shown in FIG. 6, both the odor removal unit 30 and ozone removal unit 40 are operated in the cooking device 100 during cooking. However, the present invention is not limited thereto, but instead the odor removal unit 30 and ozone removal unit 40 may be operated before and after cooking. As an example, the odor removal unit 30 and ozone removal unit 40 may be operated to clean the inside of the cooking device after cooking. Also, the odor removal unit 30 and ozone removal unit 40 may be operated before cooking, so that the odor and odor-producing materials from previous food may not be absorbed by the present food.

Figure 7:
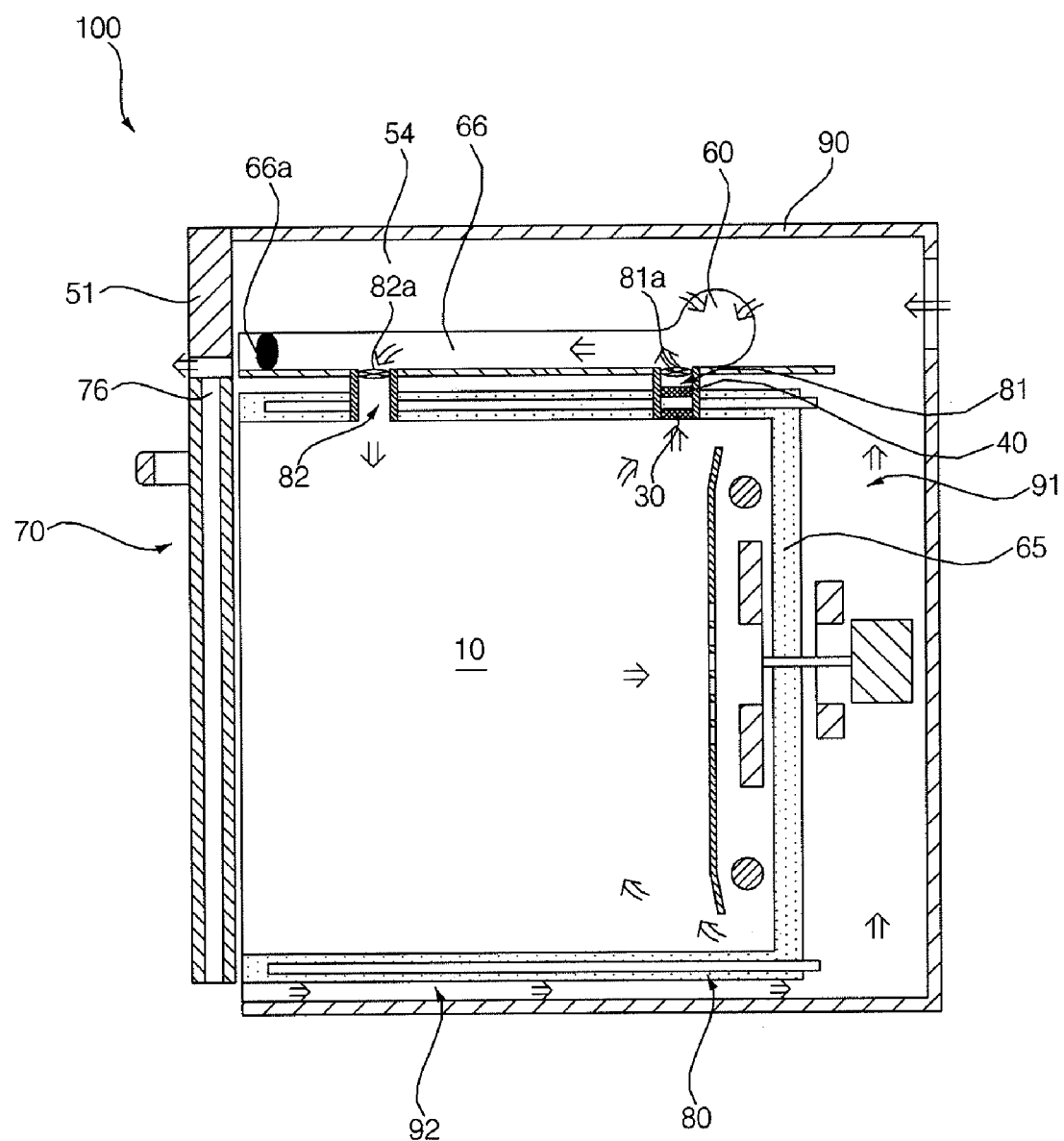
FIG. 7 is a view schematically illustrating a circulation of air in the cooking device of FIG. 2 before or after cooking.

FIG. 7 shows a circulation of a gas in the cooking device 100 before and after cooking. The fan 62 rotates to cause an air circulation in the cooking space 10. The first valve 81a and the second valve 82a are opened, and the duct valve 66a is closed. The rotation of the fan 62 makes the odor and odor-producing materials from the cooking space 10 mix with the air in the inside of the cooking space 10 and the mixed air flowed through the first communicating portion 81.

Then, the odor removal unit 30 and ozone removal unit 40 operate in the first communicating portion 81 to remove the odor and odor-producing materials and remaining ozone.

The gas that passed through the odor removal unit 30 goes through the duct 66, and then returns to the cooking space 10 through the second communicating portion 82. Accordingly, the odor and odor-producing materials remaining in the cooking space 10 may be removed while repeatedly circulating through the first communicating portion 81, the duct 66, and second communicating portion 82, which provides for complete removal of the odor and odor-producing materials. The ratio of removing the odor and odor-producing materials may be controlled by adjusting the circulatory time of the gas.

While the invention has been shown and described with reference to certain exemplary embodiments thereof, it will be understood by those skilled in the art that various changes in form and details may be made therein without departing from the spirit and scope of the invention as defined by the appended claims.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The above disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

Although the invention has been described with reference to several exemplary embodiments, it is understood that the words that have been used are words of description and illustration, rather than words of limitation. As the present invention may be embodied in several forms without departing from the spirit or essential characteristics thereof, it should also be understood that the above-described embodiments are not limited by any of the details of the foregoing description, unless otherwise specified. Rather, the above-described embodiments should be construed broadly within the spirit and scope of the present invention as defined in the appended claims. Therefore, changes may be made within the metes and bounds of the appended claims, as presently stated and as amended, without departing from the scope and spirit of the invention in its aspects.

What is claimed is:

1. A cooking device comprising:
   an inner case;
   a cooking chamber within the inner case; and
   an odor removal unit configured to generate a plasma discharge for removing odor-producing materials from the cooking chamber,
   wherein the inner case comprises an opening for exhausting air containing odor-producing materials from the cooking chamber to the outside, and the odor removal unit is arranged to correspond to the opening.

2. The cooking device of claim 1, wherein the plasma discharge generates ozone and/or ions for removing the odor-producing materials.

3. The cooking device of claim 1, wherein the odor-producing materials are removed from the air while passing through the odor removal unit, after which the air is mixed with air from the outside, and then discharged to the outside.

4. The cooking device of claim 1, further comprising:
   an outer case containing the inner case and the odor removal unit, wherein air containing odor-producing materials circulates in the outer case, so that the odor-producing materials are removed from the air while passing through the odor removal unit.

5. The cooking device of claim 1, further comprising: a controller that selectively controls the operation of the odor removal unit.

6. The cooking device of claim 1, wherein the cooking device is a microwave oven.

7. A cooking device comprising:
   an inner case;
   a cooking chamber within the inner case;
   an odor removal unit configured to generate a plasma discharge for removing odor-producing materials from the cooking chamber; and
   an outer case containing the inner case and the odor removal unit,
   wherein air containing odor-producing materials circulates in the outer case, so that the odor-producing materials are removed from the air while passing through the odor removal unit, and
   wherein the inner case comprises a first opening for arranging the odor removal unit and a second opening connecting the cooking chamber with the outside of the cooking chamber.

8. The cooking device of claim 7, wherein the air is discharged to the outside of the cooking chamber through the first opening, and then returns to the inside of the cooking chamber through the second opening.

9. The cooking device of claim 8, wherein the second opening is configured to be closed during cooking of food in the cooking chamber so as not to return air to the inside of the cooking chamber, and opened before or after cooking so as to return air to the inside of the cooking chamber.

10. The cooking device of claim 7, further comprising:
    a first valve configured to selectively open and close the first opening; and
    a second valve configured to selectively open and close the second opening.

11. A cooking device comprising:
    an inner case;
    a cooking chamber within the inner case;
    an odor removal unit configured to generate a plasma discharge for removing odor-producing materials from the cooking chamber; and
    a controller that selectively controls the operation of the odor removal unit,
    wherein the controller automatically operates the odor removal unit based on cooking information of the food.

12. The cooking device of claim 11, wherein the cooking information comprises a plurality of cooking modes of the cooking device, and the controller automatically operates the odor removal unit based on the plurality of cooking modes.

13. The cooking device of claim 12, wherein the plurality of cooking modes are classified into a plurality of groups based on the expected discharge amount of the odor-producing materials, such that for groups having a relatively large expected discharge amount of the odor-producing materials, the controller increases the duration of the operation time of the odor removal unit and/or increases the amount of power supplied to the odor removal unit.

14. A cooking device comprising:
an inner case;
a cooking chamber within the inner case;
an odor removal unit configured to generate a plasma discharge for removing odor-producing materials from the cooking chamber;
an input unit configured to receive instructions input by a user; and
a controller operating the odor removal unit based on the instructions input through the input unit.

15. A cooking device comprising:
an inner case;
a cooking chamber within the inner case;
an odor removal unit configured to generate a plasma discharge for removing odor-producing materials from the cooking chamber,
wherein the plasma discharge generates ozone and/or ions for removing the odor-producing materials; and
an ozone removal unit configured to remove residual ozone remaining in the air downstream from the odor removal unit.

16. A cooking device comprising:
an inner case;
a cooking chamber within the inner case; and
an odor removal unit configured to generate a plasma discharge for removing odor-producing materials from the cooking chamber,
wherein the odor removal unit comprises, a first discharge electrode and a second discharge electrode spaced from each other to generate the plasma discharge, and a dielectric layer interposed between the first discharge electrode and the second discharge electrode.

17. The cooking device of claim 16, wherein the first discharge electrode is applied with a voltage, and the second discharge electrode is grounded.

* * * * *